United States Patent [19]

Takao et al.

[11] 4,107,019
[45] Aug. 15, 1978

[54] SOLID ELECTROLYTE THIN FILM OXYGEN SENSOR HAVING THIN FILM HEATER

[75] Inventors: Hiroshi Takao, Kamakura; Kazuo Matoba, Yokosuka, both of Japan

[73] Assignee: Nissan Motor Company, Limited, Yokohama, Japan

[21] Appl. No.: 841,973

[22] Filed: Oct. 13, 1977

[30] Foreign Application Priority Data

Oct. 14, 1976 [JP] Japan .................................. 51-122298

[51] Int. Cl.² ............................................ G01N 27/46
[52] U.S. Cl. ................................................ 204/195 S
[58] Field of Search ............. 204/195 S, 1 S; 60/276; 123/119 E; 324/29

[56] References Cited

U.S. PATENT DOCUMENTS

| | | | |
|---|---|---|---|
| 3,871,981 | 3/1975 | Flais et al. | 204/195 S |
| 3,978,006 | 8/1976 | Topp et al. | 204/195 S X |
| 4,001,756 | 1/1977 | Heijne | 204/195 S X |

Primary Examiner—G. L. Kaplan
Attorney, Agent, or Firm—Bacon & Thomas

[57] ABSTRACT

An oxygen sensor made up of an oxygen concentration cell which as a stratiform structure and includes a thin film of an oxygen ion conductive solid electrolyte and a thin layer of a material serving as the source of a reference oxygen partial pressure such as a Ni-NiO system, an electrically nonconductive base plate which supports thereon the cell, and a thin metal layer embedded in the base plate as a resistance heating element for heating the solid electrolyte film.

10 Claims, 6 Drawing Figures

SOLID ELECTROLYTE THIN FILM OXYGEN SENSOR HAVING THIN FILM HEATER

BACKGROUND OF THE INVENTION

This invention relates to a oxygen sensor which is in principle an oxygen concentration cell having a solid electrolyte layer and useful for detecting oxygen concentration in gases and liquids, and more particularly to an oxygen sensor of this type having a construction suitable for use in either an intake system or an exhaust system of an automotive internal combustion engine.

Oxygen sensors of this type are of practical use for detecting oxygen content of, for example, molten metals and combustion engine exhaust gases. For this type of oxygen sensors, a reference oxygen partial pressure needs to be applied to one side of a solid electrolyte layer while the other side is exposed to a substance subject to measurement and the solid electrolyte layer must be kept at elevated temperatures to maintain the conductivity of the solid electrolyte at a high level. When the measurement of oxygen content of a gas whose temperature is not sufficiently high either constantly or temporarily, therefore, the oxygen sensor for the measurement needs to comprise a certain heating means. For this purpose, it is a usual practice to adopt a resistance heating method by the provision of a heater wire around the solid electrolyte layer so as to accomplish the heating by radiation and convection as shown, for example, in Japanese patent applications: Publication No. 47(1972)-28957, Publication No. 49(1974)-19839 and Public Disclosure No. 47(1972)-37599.

The resistance heating method in conventional oxygen sensors, however, is not satisfactory in efficiency, particularly when used in a gas stream of a large flow rate since a large amount of heat generated by the heater is carried away by the gas stream without being transferred to the electrolyte layer. The application of a greatly increased current to the heater as compensation for the heat loss is uneconomical and requires the provision of an unduly big power supply. Accordingly the conventional resistance heating method is unsuitable for practical use on vehicles typified by automobiles, so that the measurement of oxygen content of an air-fuel mixture in a fuel supply systems for automotive internal combustion engines as the basis for a precise control of the air/fuel ratio of the mixture has encountered a difficulty.

When an oxygen sensor comprising a solid electrolyte oxygen concentration cell is exposed at one side of its solid electrolyte layer to a substance whose oxygen partial pressure is $P_1$ and at the other side to a reference substance providing a reference oxygen partial pressure $P_2$, the cell develops an electromotive force (EMF) E across the electrolyte layer determined by the Nernst equation:

$$E = (RT/4F) \log_e (P_1/P_2) \quad (1)$$

where R is the gas constant, T represents an absolute temperature at which the solid electrolyte layer is kept, and F is the Faraday constant.

A practical output voltage V of the cell differs from the potential E since the cell has an internal resistance $R_1$ and the potential E is detected by means of an instrument having an input resistance $R_2$. The practical output voltage V is given by $$V = [R_2/(R_1 + R_2)] E \quad (2)$$

The solid electrolyte in the cell has such a great resistivity that the internal resistance $R_1$ of the cell can be regarded nearly equal to the resistance r of the solid electrolyte layer, given by $$r = (1/\rho) \cdot (t/S) \quad (3)$$

where $\rho$ is the conductivity of the solid electrolyte, $t$ is the thickness of the solid electrolyte layer and S is an effective surface area of the same layer. The conductivity depends on the degree of ease in the migration of oxygen ions in the solid electrolyte and hence is a function of temperature:

$$\rho = \rho_o \exp(-[Q/RT]) \quad (4)$$

where $\rho_o$ is a constant specific to each material, Q is another constant which is specific to each material and implies an activation energy for diffusion of ions, and both R and T represent the same as in Equation (1). Accordingly Equation (2) for the output voltage V is rewritten as $$V = \frac{R_2}{R_2 + (t/S)(1/\rho_o) \exp(-Q/RT)} \cdot \frac{RT}{4F} \log_e \frac{P_1}{P_2} \quad (5)$$

Equation (5) indicates the output voltage V depends greatly on the temperature T.

Based on the recognition that a decrease in the thickness $t$ of the solid electrolyte layer (a lowering in the internal resistance $R_1$ of the cell) is effective for raising the output voltage V and for lessening the total heat capacity of the sensor (meaning more ease in raising the temperature T of the solid electrolyte), we have recently proposed an oxygen sensor of a novel construction. This oxygen sensor has a base plate of an electrically nonconductive material as a basic structural member of the sensor, a thin layer which is laid on one side of the base plate and is made of a mixture of a metal and an oxide of the metal, a thin solid elctrolyte layer formed on the metal-oxide layer and a thin and gas permeable cathode electrode layer laid on the electrolyte layer. The metal-oxide layer serves both as the source of a reference oxygen partial pressure and as the anode electrode layer though it is optional to interpose a thin metal layer as the anode electrode layer between the base plate and the metal-oxide layer. Since every component of the sensitive part of this oxygen sensor is made as a thin layer or film and the sensor includes the source of a reference oxygen partial pressure in the form of a thin layer of a solid material, the sensor can be produced as a very compact and physically strong device with a functional advantage of being quickly heatable.

SUMMARY OF THE INVENTION

It is an object of the present invention to provide an improved oxygen sensor of the oxygen concentration cell type using a solid electrolyte, which sensor is very small in the heat capacity of the oxygen concentration cell and includes a resistance heating element capable of efficiently heating the solid electrolyte exclusively by heat conduction through the interior of the sensor, so that the sensor is practicable even in a low temperature gas stream.

It is another object of the invention to provide an improved oxygen sensor fundamentally made up of a solid electrolyte oxygen concentration cell, which includes an oxygen-containing solid material as the source of a reference oxygen partial pressure and has its components each in the form of a thin film and as a whole in a stratiform structure, and a base plate which supports thereon the cell and has a resistance heating element in the form of a thin metal layer embedded therein.

An oxygen sensor according to the invention is of an oxygen concentration cell type and comprises a base plate of an electrically nonconductive material, a thin layer of a material which is composed of a metal and an oxide of the metal to serve as the source of a reference oxygen partial pressure laid on one side of the base plate, a thin layer of an oxygen ion conductive solid electrolyte laid on the metal-oxide layer so as to shield the metal-oxide layer entirely from the atmosphere, an electron conductive thin layer coated on the solid electrolyte layer, and a thin metal layer which has a resistance suitable as a resistance heating element and is embedded in the base plate to lie generally parallel to the solid electrolyte layer.

To afford the heater layer a suitable resistance, it is convenient to form this layer in the form of a narrow lane meandering in a horizontal plane.

In this oxygen sensor, it is possible to utilize the metal-oxide layer also as the anode electrode layer of the oxygen concentration cell without the provision of any extra conductive layer on the base plate side of the solid electrolyte layer, but optionally another electron conductive thin layer as the anode electrode layer may be interposed between the base plate and the metal-oxide layer. Also optionally, exposed surfaces of the cathode electrode layer and the solid electrolyte layer may be covered with a gas permeable protective coating of a nonconductive material.

The heater may be electrically isolated from the anode of the oxygen concentration cell, but it is possible to electrically connect the heater layer at its one end with the anode to omit one of electric terminals.

An oxygen sensor according to the invention has manifold advantages as follows.

(1) Since the sensor includes an electric heater layer for heating the solid electrolyte layer, oxygen concentration in a gas can be measured by this sensor readily and accurately even when the gas is not heated above room temperature.

(2) Since the heater layer is not exposed but is completely embedded in a base plate, there is no fear that a gas subject to measurement may be ignited by the heater even when the sensor is used for the measurement of oxygen concentration in a combustible gas mixture such as an air-fuel mixture flowing in a carburetor of an automotive internal combustion engine system.

(3) Since the sensitive part of the sensor has a multilayer structure with a considerably small total thickness, the sensor can be made compact as a whole and so small in heat capacity that the heating of the sensor can be achieved with only a small power consumption.

(4) Since the sensor is very simple in its shape and construction, mass production of this sensor is quite feasible with success in a substantial reduction in the manufacturing costs.

(5) Since the sensor has an integrated structure having substantially no hollow portion, the sensor is highly resistant to mechanical shocks and vibrations and hence fully serves as a highly reliable component of a control system for an automotive engine.

DESCRIPTION OF PREFERRED EMBODIMENTS

Figure 1:
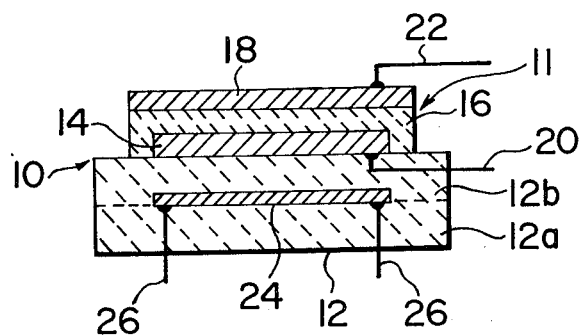
FIG. 1 shows in section a fundamental construction of an oxygen sensor according to the invention.

Referring to FIG. 1, an oxygen sensor 10 according to the invention is fundamentally made up of a sensitive part 11 having a multi-layer structure and a base plate 12 which supports on its one side the whole of the sensitive part 11 and serves as a basic structural member of the sensor 10.

The base plate 12 is of a material electrically nonconductive and stable at high temperatures and has a substantially gas impermeably solid structure. Ceramic materials such as alumina, mullite, spinel and forsterite are suitable as the material of the base plate 12.

The sensitive part 11 has an electronically conductive thin layer 14 laid on one side of the base plate 12, a thin layer 16 of a oxygen ion conductive solid electrolyte intimately and entirely covering the layer 14 and an electronically conductive thin layer 18 laid on the outer surface of the solid electrolyte layer 16. The material of the conductive layer 14 is either a mixture of a metal and an oxide of the metal or a partially oxidized metal, so that this layer 14 serves both as a cathode electrode layer and as a source of a reference oxygen partial pressure needful for the sensitive part 11 which functions as an oxygen concentration cell. Examples of (metal)-(metal oxide) systems useful as the material of the conductive and oxygen-containing layer 14 are Ni-NiO, Cd-CdO, Zn-ZnO, Cu-$Cu_2O$, Co-CoO and Cr-$Cr_2O_3$ with various metal percentages ranging from 1 to 99 Wt%. The use of a Ni-NiO system is the most preferable. The conductive layer 18 is the anode electrode layer of this cell and has a porous structure to allow a gas subject to measurement to permeate therethrough and come into contact with the surface of the solid electrolyte layer 16.

The material of the solid electrolyte layer 16 is selected from known oxygen ion conductive solid electrolytes such as $ZrO_2$ with the addition of a stabilizing oxide such as CaO, $Y_2O_3$, SrO, MgO, or $ThO_2$; $Bi_2O_3$ stabilized with $Nb_2O_5$, SrO, $WO_3$, $Ta_2O_5$ or $Y_2O_3$; $ThO_2$-$Y_2O_3$ system and CaO-$Y_2O_3$ system.

When the anode electrode layer 18 is desired to exhibit no catalytic activity on oxidation reactions, Ag, Au or SiC may be used as the material. When this layer 18 is desired to be catalytic for the oxidation of, for example, carbon monoxide and hydrocarbons contained in the exhaust gas of an internal combustion engine, the material is selected from the platinum group metals, i.e. Ru, Rh, Pd, Os, Ir and Pt, including their alloys, and alloys of a platinum group metal and a base metal.

Leads 20 and 22 are connected respectively to the cathode and anode electrode layers 14 and 18. Optionally, the anode layer 18 and the exposed regions of the solid electrolyte layer 16 may be covered with a porous protective layer (not shown in FIG. 1) of a heat-resistant and electrically nonconductive material which may be an oxide such as alumina, beryllia, zirconia, calcium-zirconate, spinel or mullite, a carbide such as silicon carbide, a nitride or a boride.

It is not a requisite that the metal-oxide layer 14 serves not only as the source of a reference oxygen partial pressure but also as the cathode electrode. A porous layer of a metal (not shown in FIG. 1) as a cathode electrode layer may be interposed between the metal-oxide layer 14 and the solid electrolyte layer 16 (then the lead 20 is connected to this cathode layer).

As an essential feature of this oxygen sensor 10, an electrically conductive thin layer 24 having a resistance suitable as an electric heater is embedded in the base plate 12 generally parallel to and at a short distance from the surface on which lies the sensitive part 11. Usually this layer 24 is formed as a narrow lane meandering in a horizontal plane to give, for example, S-shape or M-shape. Examples of metals useful as the material of the heater layer 24 are platinum, palladium, molybdenum, tungsten and tantalum, including alloys and mixtures of these metals. Various known techniques for forming a thin metal layer such as screen printing, evaporation deposition, sputtering and ion plating are applicable to the formation of this heater layer 24. A pair of leads 26 are connected to this heater layer 24 for the application of a voltage thereto. For the embedment of the heater layer 24, the base plate 12 is usually a cemented assembly of a lower layer 12a and an upper layer 12b. The heater layer 24 is formed either on the upper surface of the lower layer 12a or on the lower surface of the upper layer 12b before the cementing of the two layers 12a, 12b. The surfaces of the lower and upper layers 12a and 12b do not need to be dented because the thickness of the heater layer 24 is very small, usually less than 10μm.

It is possible to omit one of the leads 26 by connecting the cathode lead 20 not only to the cathode electrode layer 14 but also to one end of the heater layer 24 when it is intended to operate the heater layer 24 by the application of a DC voltage.

In the use of this oxygen sensor 10, a voltage is externally applied to the heater layer 24 through the leads 26 so that the heater layer 24 generates heat the amount of which is determined by the magnitude of the applied voltage and the resistance of the layer 24. Since the sensitive part 11 takes the form of a thin layer as a whole, this part 11 can be heated quickly to a temperature required for its efficient function. The anode electrode layer 18 (or the aforementioned protective coating) is exposed to a gas subject to measurement. Then the sensitive part 11, an oxygen concentration cell, develops a EMF representing the difference of the oxygen partial pressure in the gas on the interface between the anode electrode layer 18 and the solid electrolyte layer 16 from the reference oxygen partial pressure on the other side of the electrolyte layer 16 provided by the metal-oxide layer 14. This EMF is measured as a voltage between the leads 20 and 22.

Figure 2:
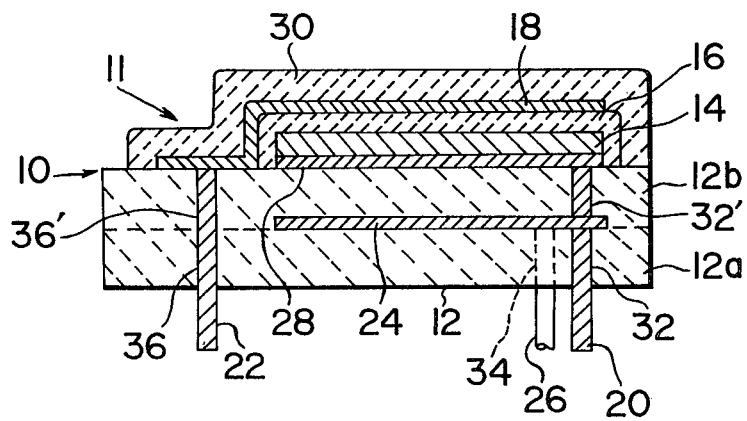
FIG. 2 is a longitudinal sectional view of an oxygen sensor as a preferred embodiment of the invention.
Figure 3:
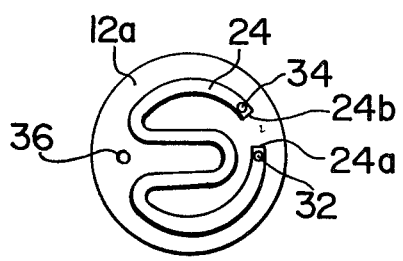
FIG. 3 is a plan view of the sensor of FIG. 2 at an early stage in the manufacture of the sensor.
Figure 4:
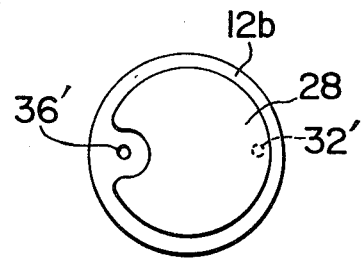
FIG. 4 is a plan view of the same sensor at a later stage in the manufacture.

The oxygen sensor 10 of the above described fundamental construction is shown in FIGS. 2–4 in a practical shape by way of example. (Both in FIG. 1 and FIG. 2, the sensitive part 11 and the heater layer 24 are illustrated with exaggeration in thickness.)

In this case the base plate 12 is a disc consisting of lower and upper discs 12a and 12b cemented together after the heater layer 24 is formed on the upper surface of the lower disc 12a. As shown in FIG. 3, the heater layer 24 takes the form of a roughly M-shaped lane in plan view and has a thickness of a few microns. The lower disc 12a has two holes 32 and 34 extending from the upper surface to the lower surface respectively at the two ends 24a and 24b of the belt-shaped heater layer 24. Another hole 36 is bored through the lower disc 12a at a location somewhat distant from the heater layer 24. The upper disc 12b has a hole 32' which extends from the upper surface to the lower surface and aligns with the hole 32 in the lower disc 12a when the two discs 12a, 12b are assembled together and another hole 36' which aligns with the hole 36 in the lower disc 12a. An electronically conductive layer 28 is laid on the upper surface of the upper disc 12b (the upper surface of the base plate 12) with a thickness of, for example, several microns to serve as the anode electrode layer of the sensor 10. As shown in FIG. 4, this conductive layer 28 has a generally circular shape containing the upper end of the hole 32' therein but is somewhat deformed such that the upper end of the hole 36' is laterally outside of this layer 28. The metal-oxide layer 14 covers the entire area of the anode electrode layer 28 and has a thickness of, for example, several microns. The solid electrolyte layer 16 is, for example, several microns thick and intimately covers not only the upper surface of the metal-oxide layer 14 but also the side surfaces of the layer 14 and the anode electrode layer 28 without covering the upper end of the hole 36'. The cathode electrode layer 18 is laid on the upper surface of the solid electrolyte layer 16 and is extended onto the upper surface of the base plate 12 so as to cover the upper end of the hole 36'. A porous protective coating 30 entirely covers the exposed surfaces of the cathode electrode layer 18 and the solid electrolyte layer 16.

The inside of the hole 32 (including the upper portion 32') is coated with a thin conductive layer (not indicated), and the lead 20 is inserted into this hole and fixed by blazing so as to make electrical connection with both the anode electrode layer 28 and the heater layer 24. In the same manner the lead 22 is inserted into the hole 36, 36' so as to make electrical connection with the cathode electrode layer 18, and lead 26 is connected to the heater layer 24 through the hole 34. In this case the lead 20 serves both as the anode lead (one of the output terminals) for the sensitive part 11 and as one of the two leads 26 in FIG. 1 for the application of a voltage to the heater layer 24.

Figure 5:
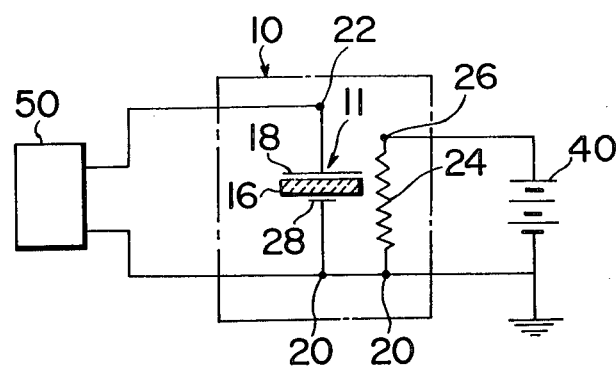
FIG. 5 is a circuit diagram showing the electrical connection for the sensor of FIG. 2.

FIG. 5 shows the manner of electrical connection for the use of the oxygen sensor 10 of FIG. 2. The leads 20 and 26 are connected to a DC power supply 40, and the leads 20 and 22 are connected to an instrument 50 for the measurement of a EMF developed by the sensitive part 11 of the sensor 10. If it is intended to use an AC voltage for heating the heater layer 24, two leads 26 independent from the anode lead 20 must be provided to the heater layer 24 as shown in FIG. 1.

EXAMPLE

The oxygen sensor 10 of FIGS. 2–4 was produced by the following procedures.

The material of the base plate 12 was a granular alumina prepared from a powdered high purity alumina by a wet granulation process using 0.5 Wt% of methyl cellulose as a binder. The granular alumina was molded into a disc of 8 mm in diameter and 1 mm in thickness as the lower part 12a of the base plate 12. The three holes 32, 34 and 36 were bored through this disc 12a as illustrated in FIG. 3 each with a diameter of about 0.5 mm.

A platinum paste was prepared by dispersing a platinum powder in a nitrocellulose lacquer, followed by dilution with cyclohexanone. This paste was applied onto the upper surface of the disc 12a by a screen printing technique to give the pattern of FIG. 3.

The upper part 12b of the base plate 12 was produced as a disc identical with the lower part 12a both in the material and dimensions, and the two holes 32' and 36' were bored as shown in FIG. 4 each with the same diameter as the corresponding hole 32 or 36 in the lower disc 12a. The aforementioned platinum paste was applied onto the lower surface of the upper disc 12b to cover a generally circular area as shown in FIG. 4 with a diameter of about 6.5 mm. Then an alumina slurry was applied to the lower surface of the upper disc 12b over the entire area, and the upper disc 12b was placed on the lower disc 12a with the printed platinum layer (24) on the upside such that the holes 32' and 36' were in alignment with the holes 32 and 36, respectively.

After drying of the thus cemented base plate 12, the above described platinum paste was applied to the inside of the holes 32 (including the upper portion 32'), 34 and 36 (including the upper portion 36'). Then the base plate 12 was heated in an electric furnace at 1800° C to accomplish sintering of the applied platinum paste and the alumina slurry. After sintering, the platinum heater layer 24 had a thickness of about 2 μm and its resistance at room temperature was about 2 ohms. The platinum anode layer 28 was about 2 μm thick.

As a first step for forming the metal-oxide layer 14, an about 5 μm thick nickel layer was laid on the upper surface of the anode layer 14 by an electroplating process using a plating bath which contained 200 g/l of nickel sulfate, 20 g/l of ammonium chloride and 15g/l of boric acid. The pH of the bath was adjusted to 6, and the plating was conducted for 1 hr at a current density of 0.5 A/dm$^2$, maintaining the bath temperature at room temperature. Thereafter the base plate 12 was heated in air using an electric furnace at 400° C for 30 min, so that the plated nickel coating was partly oxidized and turned into the oxygen-source layer 14 of a Ni-NiO system.

A mixture of 30 mol% calciumzirconate and 70 mol% zirconia was thoroughly pulverized and sieved to obtain a fine powder smaller than about 10 μm in particle size, and this powder was dispersed in a nitrocellulose lacquer to give a paste. The exposed surfaces of the Ni-NiO layer 14 and the anode layer 28 were entirely coated with this paste such that the shortest distance from the upper end of the hole 36' to this coating was about 1 mm. Then the base plate 12 was heated in an electric furnace for 1 hr at 1400° C to accomplish sintering of the coated paste. As a result, the coated paste turned into the solid electrolyte layer 16 which was composed of 85 mol% $ZrO_2$ and 15 mol% CaO and had a thickness of about 30 μm. Then the outer surfaces of the solid electrolyte layer 16 and the exposed region of the upper surface of the base plate 12 were coated with the above described platinum paste, followed by heating for 1 hr at 1300° C. The cathode electrode layer 18 thus formed was about 2 μm thick.

The outer surfaces of the sensitive part 11 were covered with the porous protective coating 30 formed to a thickness of about 50 μm by plasma spraying of an alumina powder.

A copper wire of 0.4 mm in diameter was used as each of the leads 20, 22 and 26. The leads 20, 22 and 26 inserted respectively into the holes 32, 34 and 36 were fixed to the base plate 12 and electrically connected with the anode layer 28, cathode layer 18 and heater layer 24 by the use of a silver-base blazing solder.

Figure 6:
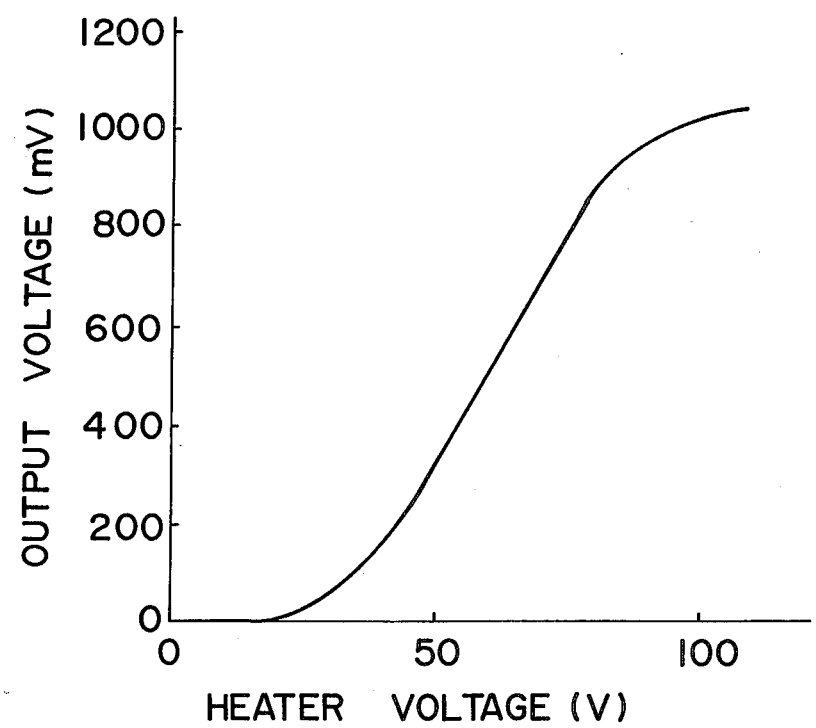
FIG. 6 is a graph showing the output voltage of an oxygen sensor according to the invention as a function of a voltage applied to a heater layer of the sensor.

The effect of the heater layer 24 on the output characteristic of the oxygen sensor 10 produced in this example in the atmospheric air at room temperature was examined by varying the magnitude of voltage applied to the heater layer 24 with the employment of the electrical connection of FIG. 5. The input resistance of the measurement instrument 50 was 1 MΩ. The result of this experiment is graphically presented in FIG. 6, demonstrating a practical applicability of this sensor 10 to the measurement of oxygen concentration in a room temperature gas.

As mentioned hereinbefore, the heater layer 24 can be formed also by a thin-film forming method different from the combination of screen printing and baking employed in the above example. Similarly, every layer in the sensitive part 11 can be formed in a way different from the way adopted in the above example. For instance, the repetition of the above example except for the formation of the Ni-NiO layer 14 by a sputtering technique using a mass of a compacted powder mixture of Ni and NiO as the target gave the same result.

Partial oxidation of a metal layer as a method of forming the metal-oxide layer 14 is of practical use also for metals other than nickel. The replacement of the NI-NiO layer 14 in the above example by a Cr-$Cr_2O_3$ layer formed through the following procedures gave an oxygen sensor whose output characteristic in air with respect to the voltage applied to the heater layer 24 was generally similar to that of the sensor produced in the above example though there were differences in the absolute values for the output voltage due to a difference in equilibrium oxygen partial pressure between the Ni-NiO system and the Cr-$Cr_2O_3$ system. The first procedure was electroplating conducted for 1 hr at a current density of 50 A/dm$^2$ using a plating bath which contained 200 g/l of $Cr_2O_3$ and 2 g/l of $H_2SO_4$ and was maintained at room temperature. As a subsequent procedure, the plated chromium layer was partially oxidized by heating in air for 1 hr at 800° C.

What is claimed is:
1. An oxygen sensor of an oxygen concentration cell type, comprising:
  a base plate of an electrically nonconductive material;
  a thin layer laid on one side of said base plate, said thin layer being of a material which is composed of a metal and an oxide of said metal and serves as the source of a reference oxygen partial pressure;
  a thin layer of an oxygen ion conductive solid electrolyte laid on the metal-oxide layer so as to entirely shield the metal-oxide layer from the atmosphere;
  an electron conductive and gas permeable thin layer coated on the solid electrolyte layer; and
  a thin metal layer which has a resistance suitable as a resistance heating element and is embedded in said base plate to lie generally parallel to the solid electrolyte layer.

2. An oxygen sensor as claimed in claim 1, wherein said thin metal layer takes the form of a narrow lane meandering in a horizontal plane.

3. An oxygen sensor as claimed in claim 2, wherein said thin metal layer is made of a resistive metal selected from the group consisting of platinum, palladium, molbydenum, tungsten and tantalum, including alloys and mixtures thereof.

4. An oxygen sensor as claimed in claim 2, wherein said base plate is an assembly of a lower plate/and an upper plate fixedly placed on one side of said lower plate, said thin metal layer being formed on one of the upper surface of said lower plate and the lower surface of said upper plate before the assemblage of the lower and upper plates.

5. An oxygen sensor as claimed in claim 2, further comprising another electron conductive thin layer interposed between said one side of said base plate and the metal-oxide layer.

6. An oxygen sensor as claimed in claim 5, wherein said thin metal layer is electrically connected at one end thereof to said another electron conductive thin layer.

7. An oxygen sensor as claimed in claim 5, wherein the metal-oxide layer is a partially oxidized metal layer produced by plating the outer surface of said another electron conductive thin layer with a metal and then partially oxidizing the plated layer.

8. A oxygen sensor as claimed in claim 7, wherein said material of the metal-oxide layer is selected from the group consisting of a Ni-NiO system and a Cr-$Cr_2O_3$ system.

9. An oxygen sensor as claimed in claim 2, wherein said thin metal layer has a thickness not larger than about 10 μm.

10. An oxygen sensor as claimed in claim 2, wherein said material of the metal-oxide layer is a mixture of Ni and NiO.

* * * * *